United States Patent [19]

Beuther et al.

[11] Patent Number: 4,717,702

[45] Date of Patent: Jan. 5, 1988

[54] CATALYST FOR CONVERSION OF SYNTHESIS GAS TO DIESEL FUEL AND PROCESS FOR PREPARATION OF SUCH CATALYST

[75] Inventors: Harold Beuther, Cheswick; Charles L. Kibby, Gibsonia; T. P. Kobylinski, Prospect; Richard B. Pannell, Allison Park, all of Pa.

[73] Assignee: Shell Internationale Research Maatschappij BV, The Hague, Netherlands

[21] Appl. No.: 876,458

[22] Filed: Jun. 20, 1986

Related U.S. Application Data

[60] Division of Ser. No. 755,657, Apr. 26, 1985, Pat. No. 4,613,624, which is a continuation of Ser. No. 310,969, Oct. 13, 1981, abandoned.

[51] Int. Cl.$^4$ .................... B01J 21/04; B01J 23/10; B01J 23/74

[52] U.S. Cl. .................... 502/303; 502/302; 502/332

[58] Field of Search .................... 502/302, 303, 332

[56] References Cited

U.S. PATENT DOCUMENTS

| | | | |
|---|---|---|---|
| 3,536,632 | 10/1970 | Kroll | 502/107 |
| 4,048,250 | 9/1977 | Garwood et al. | 260/683.43 |
| 4,073,750 | 2/1978 | Yates et al. | 252/459 |
| 4,088,671 | 5/1978 | Kobylinski | 260/449.6 R |
| 4,093,029 | 6/1978 | Weisz et al. | 166/305 R |
| 4,116,995 | 9/1978 | Kobylinski et al. | 260/449.6 M |
| 4,142,962 | 3/1979 | Yates et al. | 208/109 |
| 4,192,777 | 3/1980 | McVicker et al. | 252/447 |
| 4,399,234 | 8/1983 | Beuther et al. | 518/715 |
| 4,413,064 | 11/1983 | Beuther et al. | 518/715 |
| 4,492,774 | 1/1985 | Kibby et al. | 518/713 |
| 4,493,905 | 1/1985 | Beuther et al. | 502/325 |
| 4,497,903 | 2/1985 | Kibby et al. | 502/85 |
| 4,585,798 | 4/1986 | Beuther et al. | 518/715 |
| 4,605,676 | 8/1986 | Kobylinski et al. | 518/700 |
| 4,605,679 | 8/1986 | Kobylinski et al. | 518/700 |
| 4,605,680 | 8/1986 | Beuther et al. | 518/715 |
| 4,613,624 | 9/1986 | Beuther et al. | 518/715 |

FOREIGN PATENT DOCUMENTS

| | | |
|---|---|---|
| 7708307 | 1/1979 | Netherlands . |
| 1512743 | 6/1978 | United Kingdom . |
| 1548468 | 7/1979 | United Kingdom . |

OTHER PUBLICATIONS

Kahn et al., "The Synthesis of Light Hydrocarbons from CO and $H_2$ Mixtures over Selected Metal Catalysts", 173rd ACS National Meeting (New Orleans 3/27/25/77, ACS Div. Fuel Chem. Prepr., 1977, 22(2), pp. 138–147.

Pannell et al., "Preprint of the Seventh International Congress on Catalysis, Jun. 30, 1980, pp. 447–459.

Huoul et al.—J. of Phys. Chem. 85(5), pp. 496–498 (1981).

Twentieth Annual Spring Symposium of the Pittsburgh Catalyst Society, Program & Abstract, Marriott Hotel, Monroeville, Pa., May 27–29, 1981.

Shah and Perotta, "Ind. Eng. Chem., Prod. Res. Dev.", 1976, 15(2), pp. 123–130.

Dent et al., 175th ACS Natl. Mtg. (Anaheim, Calif. 3/12–17/78), "ACS Div. Pet. Chem. Prepr.", 1978, 23(2), 502–12.

Borhard et al., "Ind. Eng. Chem. Prod. Res. Dev.", 1979, (18(1), 18–26).

*Primary Examiner*—W. J. Shine
*Attorney, Agent, or Firm*—Roylance, Abrams, Berdo & Goodman

[57] ABSTRACT

A catalyst for the conversion of synthesis gas comprising cobalt on a high surface area, high purity, low acidity alumina support of gamma-alumina, eta-alumina or mixtures thereof, whereby the catalyst is prepared by (A) impregnation of the alumina support with a non-aqueous, organic solvent impregnation solution of cobalt nitrate containing sufficient amounts of a Group IIIB or IVB metal salt to provide said catalyst with from about 0.05 to about 100 parts by weight of a Group IIIB or IVB metal oxide per 100 parts by weight cobalt, (B) reduction of the impregnated alumina support by heating, in the presence of hydrogen, at a heating rate of from about 0.5° to about 5° C. per minute to a maximum temperature in the range of 180° to about 220° C. for a hold time of 6 to about 24 hours and thereafter heating the impregnated alumina support in the presence of hydrogen while heating up to a maximum hold temperature of from about 250° to about 400° C. for a hold time of 6 to about 65 hours.

18 Claims, No Drawings

CATALYST FOR CONVERSION OF SYNTHESIS GAS TO DIESEL FUEL AND PROCESS FOR PREPARATION OF SUCH CATALYST

This is a division of application Ser. No. 755,657 filed Apr. 26, 1985, now U.S. Pat. No. 4,613,624, which was, in turn, a continuation of application Ser. No. 310,969 filed Oct. 13, 1981, now abandoned.

REFERENCES TO RELATED APPLICATIONS

U.S. Ser. No. 310,977, filed Oct. 13, 1981 entitled "FLUID BED CATALYST FOR SYNTHESIS GAS CONVERSION AND UTILIZATION THEREOF FOR PREPARATION OF DIESEL FUEL" to Harold Beuther, T. P. Kobylinski, Charles L. Kibby and Richard B. Pannell, now, U.S. Pat. No. 4,413,064.

U.S. Ser. No. 310,972, filed Oct. 13, 1981 entitled "PROCESS FOR PREPARING GASOLINE RANGE HYDROCARBONS FROM SYNTHESIS GAS AND CATALYST USED THEREFOR" to Harold Beuther, T. P. Kobylinski, Charles L. Kibby and Richard B. Pannell, now, U.S. Pat. No. 4,399,234.

U.S. Ser. No. 310,973, filed Oct. 13, 1981 entitled "CONVERSION OF SYNTHESIS GAS TO DIESEL OIL AND GASOLINE" to Harold Beuther, T. P. Kobylinski, Charles L. Kibby and Richard B. Pannell, now abandoned. Which are all hereby incorporated be reference.

FIELD OF THE INVENTION

This invention relates to a process for the synthesis of diesel fuel from CO and hydrogen using a cobalt-containing catalyst, the catalyst used in such process and the manufacture of such catalyst. More particularly, this invention relates to the conversion of synthesis gas to diesel fuel using a catalyst containing cobalt promoted with a Group IIIB or IVB metal oxide supported on gamma and/or eta-alumina, and to such catalyst and its manufacture using a nonaqueous, organic solvent impregnation solution.

BACKGROUND OF THE INVENTION

The growing importance of alternative energy sources has brought a renewed interest in the Fischer-Tropsch synthesis as one of the more attractive direct and environmentally acceptable paths to high quality transportation fuels. The Fischer-Tropsch synthesis involves the production of hydrocarbons by the catalyzed reaction of CO and hydrogen. Commercial plants have operated in Germany, South Africa and other parts of the world based on the use of particular catalysts. The German commercial operation, for example, concentrated on the use of a precipitated cobalt-thoria-kieselguhr fixed-bed catalyst, and a later modification where MgO, for economy reasons, replaced part of the thoria.

More recently, U.S. Pat. No. 4,088,671 to T. P. Kobylinski describes the use of a ruthenium promoted cobalt catalyst on a support, such as alumina or kieselguhr, in the synthesis of hydrocarbons from the reaction of CO and hydrogen at substantially atmospheric pressure. It was found that the addition of small amounts of ruthenium to a cobalt synthesis catalyst resulted in the substantial elimination of methane from the product, together with the production of a more saturated, higher average carbon number product. Likewise, catalyst comprising cobalt-thoria-MgO on an alumina or kieselguhr support is described in British Pat. No. 1,548,468 to Bijwaard et al for use in the Fischer-Tropsch synthesis of hydrocarbons. Aqueous solutions of metal salts were used to impregnate the support to prepare the catalyst in the aforesaid processes, and the particular nature of the support was not seen as critical.

SUMMARY OF THE INVENTION

It has now been found in accordance with the present invention, that synthesis gas consisting essentially of CO and hydrogen can be selectively converted to a product high in straight chain paraffins in the diesel fuel boiling range ($C_9$-$C_{21}$) by using a catalyst consisting essentially of cobalt and from 0 to 100 parts by weight of an oxide of a metal of either Group IIIB or Group IVB of the Periodic Chart of the Elements per 100 parts by weight of cobalt, on a high purity, high surface area, low acidity support consisting essentially of gamma-alumina, eta-alumina or mixtures thereof. The catalyst of the present invention has a hydrogen chemisorption value of from about 100 to about 300 micromol of hydrogen per gram of total catalyst measured at 25° C. Surprisingly, it was found that a catalyst consisting essentially of cobalt, preferably promoted by a Group IIIB or Group IVB metal oxide, on gamma and/or eta-alumina could be produced having improved activity and selectivity for the production of diesel fuel range hydrocarbons by preparing the catalyst of the present invention by impregnating the alumina support with a nonaqueous, organic solution of the cobalt and the Group IIIB or IVB metal oxide. It is believed that the use of an impregnation solution consisting essentially of a nonaqueous, organic solvent results in increased dispersion of the cobalt and deposition of cobalt as smaller crystallites, as indicated by the relatively high hydrogen chemisorption values, thereby resulting in a more active and more selective catalyst for the production of diesel fuel from synthesis gas.

Thus, the thoria-promoted cobalt on alumina catalyst of the present invention has a higher activity for synthesis gas conversion to hydrocarbons and a greater selectivity to form hydrocarbons boiling in the diesel fuel range than do the best cobalt/thoria/kieselguhr catalysts presently known, as well as activity superior to a comparable alumina-supported catalyst that has been impregnated using an aqueous solution. Thus, for example, the cobalt/thoria/gamma-alumina catalyst of the present invention has an activity of about 65 $cm^3$ CO converted per hour per gram of reduced catalyst at 185° C., one atmosphere pressure and a hydrogen/CO ratio of 1:1 while at a flow rate of 480 $cm^3$ per gram per hour, as compared to an activity of about 18 $cm^3$ CO converted per hour per gram for a catalyst prepared by aqueous impregnation and run under the same process conditions.

DETAILED DESCRIPTION OF THE PREFERRED EMBODIMENTS

The preferred catalyst of the present invention consists essentially of cobalt promoted by a Group IIIB or Group IVB metal oxide on gamma or eta-alumina or mixtures thereof having low acidity, high surface area and high purity.

Any suitable Group IIIB or IVB metal oxide can be employed in the catalyst of the present invention, with oxides of the actinides and lanthanides being preferred. Thus, suitable metal oxides include, for example, $Sc_2O_3$, $Y_2O_3$, $Ac_2O_3$, $Pr_2O_3$, $PrO_2$, $Nd_2O_3$, $Sm_2O_3$, $Eu_2O_3$, $Gd_2O_3$, $Tb_2O_3$, $Tb_4O_7$, $Dy_2O_3$, $Ho_2O_3$, $Er_2O_3$, $Tm_2O_3$, $Yb_2O_3$, $Lu_2O_3$, $UO_2$, $UO_3$, $U_3O_8$, $UO_4 \cdot 2H_2O$, and the like. Especially preferred metal oxides for inclusion in the catalyst of the present invention include $ThO_2$, $La_2O_3$, $CeO_2$, $ZrO_2$, $TiO_2$, $HfO_2$, and unseparated rare earth oxide mixtures high in lanthanum, praseodynium, and neodynium. The most preferred metal oxide for use in the catalyst of the present invention is thoria and reference will be hereinafter made thereto for example.

The alumina support is either gamma-alumina or eta-alumina or mixtures thereof characterized as having low acidity, a high surface area and high purity. The expression "low acidity" as used in the present application means that the present alumina support has a Brønsted acidity with $H_o \leq 1.5$ which is less than 5 micromol per gram or about $10^{16}$ acid sites per $m^2$ of surface area. The low acidity of the support of the present invention is required in order to enable the catalyst to provide a high molecular weight hydrocarbon product boiling in the diesel fuel range.

The synthesis gas conversion catalyst of the present invention has a hydrogen chemisorption value of at least 100, preferably from about 125 to about 300 especially 150 or 200 to 300 micromol hydrogen per gram of total catalyst when measured at 25° C., which values are substantially higher than achieved using an aqueous impregnation solution containing similar metals.

The surface area of the alumina support of the present invention is at least 40 or 50 square meters per gram but is not so great as to become unduly microporous so as to permit reactant materials to enter the interstices of the catalyst. A suitable surface area is from about 40 to about 250, preferably from about 150 to about 225 square meters per gram.

As indicated, the catalyst support of the present invention must be of high purity. The expression "high purity" as used in the present application means that the catalyst contains negligible amounts of sodium, sulphate, silicon, phosphates or other material having a deleterious effect on the metal dispersion or the production of high molecular weight hydrocarbon products. For impurities creating acid sites, less than 5 micromol per gram should be present (about 0.01–0.1 weight percent depending on molecular weight). The deleterious effect of acidity is isomerization and cracking of intermediate olefins, removing them from chain growth and producing a low molecular weight product.

Unlike the catalyst described in U.S. Pat. No. 4,088,671 to Kobylinski, the catalyst of the present invention does not require ruthenium to increase the average molecular weight of the hydrocarbon products. Thus, the catalyst of the present invention contains no ruthenium.

Thus, the synthesis gas conversion catalyst of the present invention can contain the Group IIIB or IVB metal oxide, e.g. thoria, in amounts of from 0 or about 0.05 to about 100 parts by weight per 100 parts by weight cobalt, preferably from about 0.5 to 25 parts per 100 parts cobalt, with from about 1 to about 10 parts by weight per 100 parts by weight cobalt being especially preferred. The relatively low levels of the Group IIIB or IVB metal oxide control residual catalyst impurities. Thus, such component can be omitted and the catalyst is still operative. In order to omit the Group IIIB or IVB metal oxide from the catalyst, it is merely omitted from the impregnation solution.

The alumina support which is composed of gamma-alumina, eta-alumina or mixtures thereof is present in an amount of from about 10 to about 10,000 parts by weight alumina per 100 parts by weight of cobalt, preferably between about 100 and about 2,000 parts of alumina per 100 parts of cobalt, with from about 200 to about 400 parts by weight of alumina per 100 parts by weight cobalt being especially preferred. Pure gamma-alumina is preferred.

The method employed to deposit the catalytic metals of the present invention onto the alumina support involves the use of a nonaqueous, organic impregnation solution consisting essentially of a soluble cobalt salt and a soluble Group IIIB or IVB salt i.e., thorium salt, in order to achieve the necessary metal loading and distribution required to provide the highly selective and active catalyst of the present invention.

Initially, the alumina support is treated by oxidative calcination of the gamma and/or eta-alumina at a temperature in the range of from about 300° to about 800° C., preferably from about 400° to about 600° C.

Meanwhile, a nonaqueous organic solvent solution of the cobalt and thoria salts is prepared. The nonaqueous organic solvent of the present invention is a non-acidic liquid which is formed from moieties selected from the group consisting of carbon, oxygen, hydrogen and nitrogen, and possesses a relative volatility of at least 0.1. The expression "relative volatility" as used in the present application is defined as the ratio of the vapor pressure of the solvent to the vapor pressure of acetone, as reference, when measured at 25° C.

Suitable solvents include, for example, ketones, such as acetone, butanone (methyl ethyl ketone); the lower alcohols, e.g., methanol, ethanol, propanol and the like; amides, such as dimethyl formamide; amines, such as butylamine; ethers, such as diethylether; hydrocarbons, such as pentane and hexane; and mixtures of the foregoing solvents.

The preferred solvent of the present invention is a mixture of ethanol and acetone, for example, in a weight ratio of about four parts acetone per part of ethanol.

The amount of solvent utilized is an amount that is at least equivalent to the pore volume of the alumina utilized, but not greater than five times the alumina pore volume. For example, a commercially available gamma-alumina useful in the present invention has a pore volume of between about 0.2 to about 0.7 cubic centimeters pore volume per gram of alumina.

Suitable cobalt salts include, for example, cobalt nitrate, cobalt acetate, cobalt carbonyl, cobalt acetylacetonate, or the like with cobalt nitrate and cobalt carbonyl [$Co_2(CO)_8$] being especially preferred. Likewise, any suitable Group IIIB or Group IVB metal salt, such as thorium nitrate, thorium acetate or the like can be employed. In general, any metal salt which is soluble in the organic solvent of the present invention and will not introduce acidity or have a poisonous effect, e.g. a halide, on the catalyst can be utilized. Thorium nitrate is especially preferred.

Next, the calcined alumina support is impregnated in a dehydrated state with the non-aqueous, organic solvent solution of the cobalt and thorium salts. Thus, the calcined alumina should not be unduly exposed to atmospheric humidity so as to become rehydrated.

Any suitable impregnation technique can be employed including techniques well known to those skilled in the art so as to distend the catalytic metals in a uniform thin layer on the catalyst support. For example, the cobalt and thoria can be deposited on the support material by the "incipient wetness" technique. Such technique is well known and requires that the volume of impregnating solution be predetermined so as to provide the minimum volume which will just wet the entire surface of the support, with no excess liquid. Alternatively, the excess solution technique can be utilized if desired. If the excess solution technique is utilized, then the excess solvent present, e.g., ethanol and acetone is merely removed by evaporation. Thus, the impregnation solution can be added in excess, namely, up to five times the pore volume of the alumina, or can be added using just enough solution to fill the pore volume of the alumina.

Next, the impregnation solution and alumina are stirred while evaporating the solvent at a temperature of from about 25° to about 45° C. until "dryness".

If additional impregnations are needed to obtain the desired metal loading, for example, when the incipient wetness technique is used, the dried catalyst is then calcined in the presence of an oxygen-containing or inert, e.g. nitrogen, gas at a temperature just sufficient to decompose the metal salts and fix the cobalt. Suitable calcination temperatures include those in the range of from about 150° to about 300° C., preferably from about 225° to about 275° C. Such impregnation, drying and calcination can be repeated until the desired metal loading is achieved. If cobalt carbonyl is employed, contact with oxygen must be avoided. Thus, the impregnated catalyst is heated to about 200° C. in an inert gas, e.g., nitrogen, or hydrogen rather than using an oxidative calcination step.

After the last impregnation sequence, the impregnated catalyst is preferably slowly reduced in the presence of hydrogen. The reduction is best conducted in two steps wherein the first reduction heating step is carried out at a slow heating rate of no more than from about 0.5° to about 5° C. per minute, preferably from about 0.5° to about 1° C. per minute up to a maximum hold temperature of 180° to about 220° C., preferably 190° to about 210° C., for a hold time of from about 6 to about 24 hours, preferably from about 16 to about 24 hours. In the second reduction heating step, the catalyst can be heated at from about 5° to about 20° C. per minute, preferably from about 5° to about 10° C. per minute to a maximum hold temperature of from about 250° or 300° up to about 400° C., preferably from about 350° to about 400° C. for a hold time of 6 to about 65 hours, preferably from about 16 to about 24 hours. Although pure hydrogen can be employsed for this reduction step, a mixture of hydrogen and nitrogen can be utilized in order to slowly reduce the catalyst. For example, the reduction step can be conducted initially using a gaseous mixture comprising 5% hydrogen and 95% nitrogen, and thereafter, the concentration of hydrogen can be gradually increased until pure hydrogen is obtained so as to slowly reduce the catalyst. Such slow reduction is particularly desirable when the metal salts utilized in the impregnation step are nitrates so as to avoid the dangers involved with an exothermic reaction in which nitrates are given off. Thus, the slow reduction may involve the use of a mixture of hydrogen and nitrogen at 100° C. for about one hour; increasing the temperature 0.5° C. per minute until a temperature of 200° C.; holding that temperature for approximately 30 minutes; and then increasing the temperature 1° C. per minute until a temperature of 350° C. is reached and then continuing the reduction for approximately 16 hours. Such slow reduction process is not required when the cobalt salt is not a nitrate, e.g. cobalt acetate. A zero valent cobalt compound such as cobalt carbonyl can be activated by heating to 200° C. in pure hydrogen overnight.

It is preferred to omit the calcination step following the last impregnation and subject the impregnated catalyst directly to the slow reduction process.

The catalyst of the present invention has an average particle diameter which depends upon the type of reactor used of from about 0.01 to about 6 millimeters; preferably from about 1 to about 6 millimeters for a fixed bed; preferably about 0.02 to about 0.15 being preferred for a fluidized bed and from about 0.01 to about 0.05 millimeters for a slurry.

The charge stock used in the process of this invention is a mixture of CO and hydrogen. The source of the CO and hydrogen to be used in the charge stocks for this invention is not critical and can be obtained, for example, by (i) the oxidation of coal or other forms of carbon with scrubbing or other forms of purification to yield the desired mixture of CO and $H_2$ or (ii) the reforming of natural gas. $CO_2$ is not a desirable component of the charge stocks for use in the process of this invention, but it may be present as a diluent gas. Sulfur compounds in any form are deleterious to the life of the catalyst and should be removed.

The molar ratio of hydrogen to CO in the charge stock can be, for example, from about 0.5:1 to about 4:1 or higher, e.g., 10:1, preferably, from about 1:1 to about 2.5:1, with 1.5:1 to about 2:1 being especially preferred.

The reaction temperature is suitably from about 160° to about 350° C., preferably from about 175° to about 250° C., and most preferably from about 185° to about 215° C. The total pressure is from about 1 to about 100 atmospheres, preferably from about 1 to about 50 atmospheres, and most preferably from about 1 to about 20 atmospheres. The hydrogen partial pressure is from about 0.1 to about 30 atmospheres, preferably from about 0.5 to about 25 atmospheres, and most preferably from about 1 to about 20 atmospheres.

The gaseous hourly space velocity based upon the total amount of feed is less than 20,000 volumes of gas per volume of catalyst per hour, preferably from about 100 to about 5,000 v/v/hour, with from about 200 to about 2,500 v/v/hour being especially preferred. If desired, pure synthesis gas can be employed or, alternatively, an inert diluent, such as nitrogen, $CO_2$, methane, steam or the like can be added. As used herein, the expression "inert diluent" indicates that the diluent is non-reactive under the reaction conditions herein disclosed or is a normal reaction product.

The synthesis gas reaction using the catalysts of this invention can occur in a fixed, fluid or moving bed type of operation, and the type of operation would not appear to be critical. However, a fixed-bed operation is preferred, and normally the charge gases would be passed downflow through the bed of catalyst and the reaction product would be collected by suitable condensation techniques, after which the products can be separated by fractionation or otherwise.

The invention will be further described with reference to the following experimental work.

EXAMPLE 1

Catalysts of varying composition were made by impregnating pure gamma-alumina (commercially available from Ketjen as CK-300) that had been sieved to pass 100 mesh (0.15 millimeter) and calcined for two hours at 600° C., by a single step, nonaqueous, "wet" impregnation using cobalt nitrates [$Co(NO_3)_2 \cdot 6H_2O$]

and thorium nitrates [$Th(NO_3)_4 \cdot 4H_2O$] from acetone-ethanol solution in a ratio of acetone/ethanol of approximately 2.5:1. Excess solvent was removed by evaporation at a reduced pressure of approximately 0.01 atmosphere and 25°–30° C. in a rotary evaporator. The catalysts were dried at a temperature of 90° C. with moderate stirring. Melting of the nitrate salts and evolution of water occurred at approximately 50°–60° C. After the water had evolved, the catalyst appeared to be dry.

Prereduction and passivation of the impregnated catalysts were conducted using pure hydrogen at the rate of 720 cm$^3$/gram/hour. The impregnated catalysts were heated to 100° C. at the rate of 5° C. per minute and then maintained at that temperature for about one hour. Next, the catalysts were heated at the rate of 5° C. per minute to a temperature of 200° C. and then held at 200° C. for approximately sixteen hours. The catalysts were then heated at the rate of 10° C. per minute until a temperature of 360° C. was reached and then held at that temperature for twenty-two hours. Next, the catalysts were cooled to below 200° C., purged with nitrogen and further cooled. Air was bled into the nitrogen flow at approximately 1 cubic centimeter of air in 50 cubic centimeters of nitrogen per minute per 5 grams of catalyst for a period of sixteen hours.

Catalysts A–E were prepared having the compositions shown in Table I:

TABLE I

| Catalyst | Composition (Parts by Weight) | | | Weight % Cobalt | |
|---|---|---|---|---|---|
| | Co | ThO$_2$ | Al$_2$O$_3$ | Reduced | Reoxidized |
| A | 100 | 9 | 100 | 47.85 | 40.78 |
| B | 100 | 27 | 100 | 44.05 | 37.99 |
| C | 100 | 9 | 300 | 24.45 | 22.46 |
| D | 100 | 27 | 300 | 23.42 | 21.59 |
| E | 100 | 18 | 200 | 31.44 | 28.23 |

In order to determine cobalt dispersion, hydrogen chemisorption was measured after reductions at 50° C. intervals, from 200° C. to 400° C., for 16 hours at 175 cm H$_2$/gram/hour. The chemisorption isotherms were measured at 25° C. after a one hour equilibration at a H$_2$ pressure of about 500 torr (65 kPa); the zero pressure intercept extrapolated from data points about 100 torr was taken as the amount chemisorbed. The results are shown in Table II:

TABLE II

| | Hydrogen Sorbed at 25° C.[1] (micromol per gram) | | | | | |
|---|---|---|---|---|---|---|
| | Reduction Temperature, °C. | | | | | H/Co |
| Catalyst | 200 | 250 | 300 | 350 | 400 | (350° C. Reduction) |
| A | 69 | 89 | 102 | 114 | 116 | .028 |
| B | 95 | 118 | 134 | 141 | 135 | .038 |
| C | 64 | 112 | 165 | 198 | 177 | .095 |
| D | 27 | 66 | 115 | 174 | 153 | .087 |
| E | 51 | 96 | 154 | 176 | 148 | .066 |
| Avg (ABCD) | (64) | (96) | (127) | (157) | (145) | (.062) |

[1]Intercept values for 100–500 mm Hg data, based on weights of reduced catalysts.

The greatest sorption capacity was developed at 350° C. Assuming complete reduction at that temperature, and one hydrogen atom per surface cobalt atom, the values in the last column of Table II estimate the cobalt metal dispersions. The variation with alumina content is nearly linear, from 0.03 at Al$_2$O$_3$/Co=1 to 0.09 at Al$_2$O$_3$/Co=3. The effect of thoria is negligible (about equal to experimental error). The average sorption value for catalysts A–D, with high or low Al$_2$O$_3$ or ThO$_2$ levels, was close to that for catalyst E with intermediate levels of ThO$_2$ and Al$_2$O$_3$.

EXAMPLES 2–6

A series of runs were conducted using Catalyst A (100Co/9ThO$_2$/100Al$_2$O$_3$) having an average particle size of about 0.4–1.0 millimeter wherein 0.5 gram samples of the prereduced catalyst were initially heated to a temperature of 360° C. in chemically pure hydrogen flowing at the rate of 2400–6000 cm$^3$/gram/hour at the rate of 5° C. per minute for a one hour period, and then held for 65 hours at 360° C.

The hydrogen flow was then reduced to 240 cm$^3$/gram/hour and an equal flow of carbon monoxide was initiated. For those runs where the molar ratio of hydrogen/CO is 2:1, the hydrogen flow rate was increased to 480 cm$^3$/gram/hour.

Sampling was conducted periodically to analyze the products. The conditions utilized in each run and the product distribution is set forth in Table III:

TABLE III

| Ex. No. | 2 | 3 | 4 | 5 | 6 |
|---|---|---|---|---|---|
| Temp., °C. | 175 | 185 | 195 | 205 | 195 |
| H$_2$/CO | 1:1 | 1:1 | 1:1 | 1:1 | 2:1 |
| CO Flowrate (cm$^3$/gram/hour) | 275 | 275 | 275 | 275 | 275 |
| CO Conversion Rate (cm$^3$/gram/hour) | | | | | |
| To CO$_2$ | nil | 1.6 | 6.6 | 8.5 | 2.6 |
| To Hydrocarbons | 36 | 46 | 67 | 88 | 111 |
| CO Conversion (Percent) | 13 | 17 | 27 | 35 | 41 |
| Product Distribution (Carbon Atom %) | | | | | |
| CH$_4$ | 7 | 6 | 6 | 8 | 15 |
| C$_2$–C$_4$ | 11 | 7 | 8 | 11 | 15 |
| C$_5$–C$_8$ | 26 | 28 | 30 | 33 | 34 |
| C$_9$–C$_{20}$ | 56 | 56 | 54 | 41 | 34 |
| C$_{21}$+ | nil | 3 | 2 | 7 | 2 |

As seen in Table III, as the temperature is increased from 175° C. to 205° C. the CO conversion increases from 13% to 35%. However, the selectivities to C$_9$–C$_{20}$ range product, i.e. diesel fuel, are approximately 55% of the CO converted at a ratio of H$_2$/CO=1 at temperatures of about 175° to 195° C. Selectivity to the C$_9$–C$_{20}$ product drops off to 41% at 205° C. Such selectivities are higher than expected for a chain growth reaction in which chain growth probabilities are independent of chain length.

EXAMPLES 7–11

The procedure of Examples 2–6 was repeated using catalyst B of Example 1 (100Co/27ThO$_2$/100Al$_2$O$_3$) having a particle size of 0.4–1.0 millimeters.

The conditions and product distributions obtained are set forth in Table IV:

TABLE IV

| Ex. No. | 7 | 8 | 9 | 10 | 11 |
|---|---|---|---|---|---|
| Temp., °C. | 175 | 185 | 195 | 205 | 195 |
| H$_2$/CO | 1:1 | 1:1 | 1:1 | 1:1 | 2:1 |
| CO Flowrate (cm$^3$/gram/hour) | 275 | 275 | 275 | 275 | 275 |
| CO Conversion Rate (cm$^3$/gram/hour) | | | | | |
| To CO$_2$ | nil | 0.2 | 0.9 | 2.4 | 0.4 |
| To Hydrocarbons | 14 | 24 | 35 | 48 | 78 |
| CO Conversion (Percent) | 5 | 10 | 13 | 18 | 28 |

TABLE IV-continued

| Ex. No. | 7 | 8 | 9 | 10 | 11 |
|---|---|---|---|---|---|
| Product Distribution (Carbon Atom %) | | | | | |
| $CH_4$ | 7 | 6 | 7 | 8 | 11 |
| $C_2$–$C_4$ | 10 | 7 | 9 | 10 | 10 |
| $C_5$–$C_8$ | 30 | 30 | 30 | 31 | 27 |
| $C_9$–$C_{20}$ | 53 | 44 | 42 | 37 | 45 |
| $C_{21}+$ | nil | 13 | 12 | 25 | 7 |

The results set forth in Table IV indicate that the selectivities to $C_9$–$C_{20}$ range product are slightly lower when using the catalyst having thoria present increased by a factor of 3.

EXAMPLES 12–16

The procedure described in Examples 2–6 was repeated using catalyst C of Table I (100Co/9ThO$_2$/300Al$_2$O$_3$) having an average particle size of about 0.3–0.4 millimeter. The conditions used in these examples and the product distributions obtained are set forth in Table V:

TABLE V

| Ex. No. | 12 | 13 | 14 | 15 | 16 |
|---|---|---|---|---|---|
| Temp., °C. | 175 | 185 | 195 | 205 | 195 |
| $H_2$/CO | 1:1 | 1:1 | 1:1 | 1:1 | 2:1 |
| CO Flowrate (cm$^3$/gram/hour) | 270 | 270 | 270 | 335 | 270 |
| CO Conversion Rate (cm$^3$/gram/hour) | | | | | |
| To $CO_2$ | nil | 1.4 | 2.4 | 3.5 | 2.4 |
| To Hydrocarbons | 34 | 66 | 87 | 119 | 102 |
| CO Conversion (Percent) | 13 | 24 | 32 | 35 | 38 |
| Product Distribution (Carbon Atom %) | | | | | |
| $CH_4$ | 4 | 4 | 5 | 5 | 14 |
| $C_2$–$C_4$ | 5 | 5 | 6 | 7 | 13 |
| $C_5$–$C_8$ | 25 | 26 | 26 | 26 | 36 |
| $C_9$–$C_{20}$ | 65 | 62 | 53 | 53 | 33 |
| $C_{21}+$ | 1 | 3 | 10 | 9 | 4 |

The results shown in Table V indicate that this catalyst wherein the amounts of cobalt and thoria relative to alumina have been decreased is extremely active having a high conversion to hydrocarbons with a concommitant high selectivity to $C_9$–$C_{20}$ hydrocarbons in the diesel fuel boiling range. Thus, the selectivity to $C_9$–$C_{20}$ hydrocarbons is in the 50–65% range and, for example, comparing the selectivity of Example 12 (65%) with that of Example 2 (56%), it is seen that a 16% increase in selectivity was achieved using a catalyst containing a three-fold increase in alumina relative to the cobalt and thoria present.

EXAMPLES 17–21

The procedure used in Examples 2–6 is repeated using catalyst D of Example 1 (100CO/27ThO$_2$/300Al$_2$O$_3$) having a particle size of 0.3–0.4 millimeter. The conditions, CO conversion and product distribution is set forth in Table VI:

TABLE VI

| Ex. No. | 17 | 18 | 19 | 20 | 21 |
|---|---|---|---|---|---|
| Temp., °C. | 175 | 185 | 195 | 205 | 195 |
| $H_2$/CO | 1:1 | 1:1 | 1:1 | 1:1 | 2:1 |
| CO Flowrate (cm$^3$/gram/hour) | 270 | 270 | 270 | 270 | 270 |
| CO Conversion Rate (cm$^3$/gram/hour) | | | | | |
| To $CO_2$ | nil | 0.4 | 1.0 | 1.6 | 0.6 |
| To Hydrocarbons | 14 | 28 | 48 | 65 | 57 |
| CO Conversion (Percent) | 5 | 10 | 18 | 25 | 21 |
| Product Distribution (Carbon Atom %) | | | | | |
| $CH_4$ | 7 | 5 | 4 | 7 | 8 |
| $C_2$–$C_4$ | 8 | 7 | 6 | 10 | 9 |
| $C_5$–$C_8$ | 30 | 23 | 22 | 32 | 30 |
| $C_9$–$C_{20}$ | 53 | 53 | 54 | 47 | 44 |
| $C_{21}+$ | 2 | 12 | 14 | 4 | 9 |

Upon comparing the selectivity to $C_9$–$C_{20}$ hydrocarbons of Table VI with the corresponding selectivities set forth in Table IV, it is seen that as the temperature is increased, the selectivity to $C_9$–$C_{20}$ hydrocarbons is significantly higher using the catalyst wherein the amount of alumina relative to the cobalt and thoria is increased. Thus, Example 19 produced a $C_9$–$C_{20}$ selectivity of 54% as compared with Example 9 in Table IV wherein identical conditions using a catalyst having a lesser amount of alumina produced a $C_9$–$C_{20}$ selectivity of 42%.

EXAMPLES 22–26

Once again following the procedure of Examples 2–6, catalyst E of Table I (100Co/18ThO$_2$/200Al$_2$O$_3$) having an average particle size of 0.4–0.6 millimeters was tested, and the particular conditions, CO conversion and product distribution are set forth in Table VII:

TABLE VII

| Ex. No. | 22 | 23 | 24 | 25[2] | 26[3] |
|---|---|---|---|---|---|
| Temp., °C. | 175 | 185 | 195 | 205 | 195 |
| $H_2$/CO | 1:1 | 1:1 | 1:1 | 1:1 | 2:1 |
| CO Flowrate (cm$^3$/gram/hour) | 155 | 155 | 270 | 610 | 270 |
| CO Conversion Rate (cm$^3$/gram/hour) | | | | | |
| To $CO_2$ | 0.2 | 1.1 | 1.6 | 2.9 | (1.3) |
| To Hydrocarbons | 19 | 41 | 61 | 79 | (120) |
| CO Conversion (Percent) | 13 | 27 | 23 | 13 | 44 |
| Product Distribution (Carbon Atom %) | | | | | |
| $CH_4$ | 4 | 5 | 6 | 8 | 9 |
| $C_2$–$C_4$ | 6 | 7 | 8 | 10 | 9 |
| $C_5$–$C_8$ | 23 | 25 | 29 | 34 | 24 |
| $C_9$–$C_{20}$ | 62 | 59 | 50 | 44 | 49 |
| $C_{21}+$ | 5 | 4 | 7 | 4 | 9 |

[2] Separate run
[3] Not aged at 205° C.

The results set forth in Table VII indicate that catalyst E has good activity and has a high degree of selectivity to $C_9$–$C_{20}$ hydrocarbons in the 50–65% range when the temperature is from 175°–195° C.

EXAMPLES 27–29

For comparative purposes a catalyst having the composition 100Co/10ThO$_2$/286Al$_2$O$_3$ prepared by impregnating gamma-alumina with an aqueous impregnation solution containing cobalt nitrate and thorium nitrate was tested using the procedure of Examples 2–6. The catalysts had an average particle size of 0.4–0.6 millimeters.

The conditions and results are set forth in Table VIII:

TABLE VIII

| Ex. No. | 27 | 28 | 29 |
|---|---|---|---|
| Temp., °C. | 175 | 185 | 195 |
| $H_2/CO$ | 1:1 | 1:1 | 1:1 |
| CO Flowrate ($cm^3$/gram/hour) | 250 | 250 | 250 |
| CO Conversion Rate ($cm^3$/gram/hour) | | | |
| To $CO_2$ | nil | 0.1 | 0.3 |
| To Hydrocarbons | 6 | 18 | 26 |
| CO Conversion (Percent) | 2 | 7 | 10 |
| Product Distribution (Carbon Atom %) | | | |
| $CH_4$ | 6 | 6 | 7 |
| $C_2$-$C_4$ | 6 | 5 | 6 |
| $C_5$-$C_8$ | 29 | 22 | 26 |
| $C_9$-$C_{20}$ | 56[4] | 60 | 53 |
| $C_{21}+$ | 3 | 7 | 8 |

[4]Catalyst run less than 24 hours.

The catalyst used in Examples 27–29 closely approximates the catalyst used in Examples 12–16. However, it is seen in Table VIII that the CO conversion to hydrocarbons is considerably below that achieved with the catalyst of Examples 12–16 wherein the catalyst was prepared using a nonaqueous impregnation solution. Thus, comparing the CO conversion rate of Example 28 (18 $cm^3$/gram/hour) with that of Example 13 (66 $cm^3$/gram/hour), it is seen that the use of the nonaqueous impregnation solution produced a catalyst providing a four-fold increase in activity. The same dramatic increase is seen upon comparing the CO conversion to hydrocarbons in Example 29 (26) with that achieved in Example 14 (87), which examples were run under the same conditions.

EXAMPLES 30–31

A catalyst was prepared using the procedure of Example 1 but having the composition 100 parts by weight cobalt and 300 parts by weight gamma-alumina, but without any thoria, i.e., the thoria salt was omitted from the impregnation solution. In addition to the reduction treatment described in Example 1, where the temperature was first held at 200° C. for 16 hours, a separate run was made where the heating rate was about 7° C. per minute to reach a first temperature hold of 250° C. The hydrogen chemisorption capacities after the first reductions and after subsequent ones at 50° C. higher intervals are shown in Table IX:

TABLE IX

| | Hydrogen Sorbed at 25° C. (micromol per gram) | |
|---|---|---|
| Ex. No. | 30 | 31 |
| Temp. Hold, °C. Reduction Temp., °C. | 200 | 250 |
| 200 | 80 | — |
| 250 | 107 | 59 |
| 300 | 167 | 119 |
| 350 | 201 | 167 |
| 400 | 192 | — |

As seen in Table IX, the higher heating rate and final temperature for the first hold (Example 31) decreased the sorption capacity about 50 micromol per gram, thus indicating the importance of reduction heating rate and temperature upon cobalt dispersion.

What is claimed is:

1. A catalyst for the conversion of synthesis gas consisting essentially of cobalt and a Group IIIB or IVB metal oxide on a high surface area, high purity, low acidity alumina support of gamma-alumina, eta-alumina or mixtures thereof, said catalyst having a hydrogen chemisorption value of about 100 to about 300 micromol of hydrogen per gram of total catalyst when measure at 25° C. said catalyst having been prepared by (A) impregnation of said alumina support with a non-aqueous, organic solvent impregnation solution of cobalt nitrate containing sufficient amounts of a Group IIIB or IVB metal salt to provide said catalyst with from about 0.05 to about 100 parts by weight of a Group IIIB or IVB metal oxide per 100 parts by weight cobalt, (B) reduction of said impregnated alumina support by heating, in the presence of hydrogen, at a heating rate of from about 0.5° to about 5° C. per minute to a maximum temperature in the range of 180° to about 220° C. for a hold time of 6 to about 24 hours and thereafter heating said impregnated alumina support in the presence of hydrogen while heating up to a maximum hold temperature of from about 250° to about 400° C. for a hold time of 6 to about 65 hours.

2. The catalyst of claim 1 wherein said catalyst contains from about 1 to about 10 parts by weight Group IIIB or IVB metal oxide per 100 parts by weight cobalt.

3. The catalyst of claim 1 wherein said metal oxide is an oxide of an actinide, a lanthanide or zirconium.

4. The catalyst of claim 1 wherein said catalyst support is gamma-alumina.

5. The catalyst of claim 1 wherein said catalyst contains between about 0.05 and about 100 parts by weight thoria per 100 parts by weight of cobalt.

6. The catalyst of claim 1 wherein said catalyst contains between about 100 to about 2,000 parts by weight of alumina per 100 parts by weight of cobalt.

7. The catalyst of claim 6 wherein said catalyst contains from about 200 to about 400 parts by weight of alumina per 100 parts by weight of cobalt.

8. The catalyst of claim 3 wherein said metal oxide is lanthana.

9. A process for the preparation of a synthesis gas conversion catalyst which process comprises
    calcining a high purity, low acidity alumina in the presence of an oxygen-containing or inert gas at a temperature in the range of from about 300° to about 800° C., said alumina being gamma-alumina, eta-alumina or mixtures thereof,
    impregnating said calcined alumina while in a dehydrated state with a non-aqueous, organic solvent impegnation solution of cobalt nitrate containing sufficient amounts of a Group IIIB or IVB metal salt to provide said catalyst with from about 0.05 to about 100 parts by weight of a Group IIIB or IVB metal oxide per 100 parts by weight cobalt, reducing said impregnated alumina support by heating in the presence of hydrogen at a heating rate of from about 0.5° to about 5° C. per minute to a maximum temperature in the range of 180° to about 220° C. for a hold time of 6 to about 24 hours, and
    heating said impregnated alumina support in the presence of hydrogen while heating up to a maximum hold temperature of from about 250° to about 400° C. for a hold time of 6 to about 65 hours.

10. The process of claim 9 wherein said metal salt is a thorium salt.

11. The process of claim 9 wherein said metal salt is a lanthanum salt.

12. The process of claim 9 wherein said solvent has a relative volatility of at least 0.1.

13. The process of claim 12 wherein said solvent is a lower alcohol.

14. The process of claim 13 wherein said alcohol is ethanol.

15. The process of claim 14 wherein said organic solvent additionally comprises acetone.

16. The process of claim 9 wherein said impregnated catalyst is subjected to at least one additional calcination step and followed by at least one additional impregnation step utilizing another portion of said nonaqueous, organic solvent impregnation solution prior to said reduction step.

17. The process of claim 16 wherein said further calcination is conducted at a temperature in the range of between about 150° to about 350° C.

18. The process of claim 9 wherein said reduction is conducted slowly by initially using a mixture of hydrogen and nitrogen and gradually decreasing the amount of nitrogen present until pure hydrogen is utilized.

* * * * *